United States Patent [19]

Fisher et al.

[11] 4,220,856

[45] Sep. 2, 1980

[54] METHOD OF ANALYSIS OF ASBESTIFORM MINERALS BY THERMOLUMINESCENCE

[75] Inventors: Gerald L. Fisher; Edward W. Bradley, both of Davis, Calif.

[73] Assignee: The United States of America as represented by the United States Department of Energy, Washington, D.C.

[21] Appl. No.: 957,617

[22] Filed: Nov. 3, 1978

[51] Int. Cl.$^2$ .......................... G01T 1/11; H05B 33/00
[52] U.S. Cl. ..................................... 250/337; 250/484
[58] Field of Search ........... 250/337, 361, 458, 461 R, 250/461 B, 484

[56] References Cited

U.S. PATENT DOCUMENTS

| | | | |
|---|---|---|---|
| 3,020,238 | 2/1962 | Munakata | 250/484 |
| 3,388,252 | 6/1968 | Medlin | 250/337 |
| 3,600,579 | 8/1971 | Carpentier et al. | 250/484 |
| 3,769,510 | 10/1973 | Kotera et al. | 250/484 |
| 3,963,439 | 6/1976 | Birks et al. | 23/230 PC |
| 3,975,637 | 8/1976 | Ikedo et al. | 250/337 |

OTHER PUBLICATIONS

Ruud et al., "Selected Area Electron Diffraction and Energy Dispersive X-ray Analysis for the Identification of Asbestos Fibers, a comparison," *Micron*, vol. 7, pp. 115-132, 1976.

Distler et al., "Thermoluminescence of Asbestos,"

USDOE Technical Report No. UCRL-51422, Fiscal Year 1973 Summary Report for the USAEC Division of Applied Technology-Environmental Analysis, Lawrence Livermore Lab., Univ. Calif., pp. 5-7, Jul. 5, 1973.

*Primary Examiner*—Alfred E. Smith
*Assistant Examiner*—Janice A. Howell
*Attorney, Agent, or Firm*—James E. Denny; Roger S. Gaither; Clifton E. Clouse, Jr.

[57] ABSTRACT

A method for the qualitative and quantitative analysis of asbestiform minerals, including the steps of subjecting a sample to be analyzed to the thermoluminescent analysis, annealing the sample, subjecting the sample to ionizing radiation, and subjecting the sample to a second thermoluminescent analysis. Glow curves are derived from the two thermoluminescent analyses and their shapes then compared to established glow curves of known asbestiform minerals to identify the type of asbestiform in the sample. Also, during at least one of the analyses, the thermoluminescent response for each sample is integrated during a linear heating period of the analysis in order to derive the total thermoluminescence per milligram of sample. This total is a measure of the quantity of asbestiform in the sample and may also be used to identify the source of the sample.

11 Claims, 15 Drawing Figures

PROCEDURE FLOW CHART

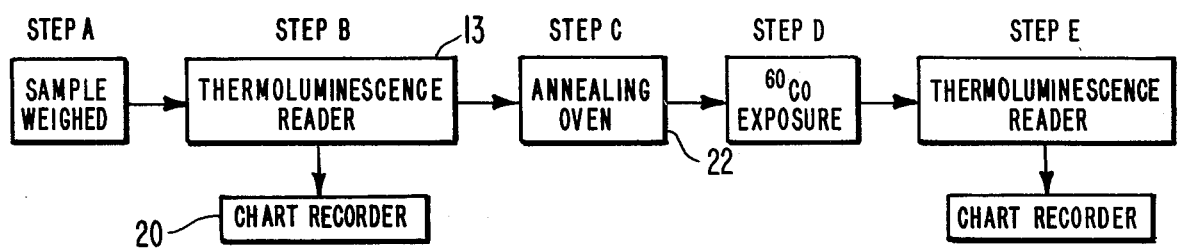
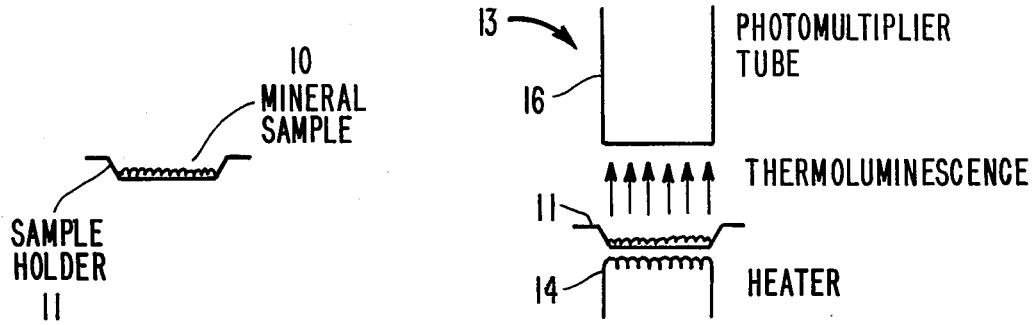
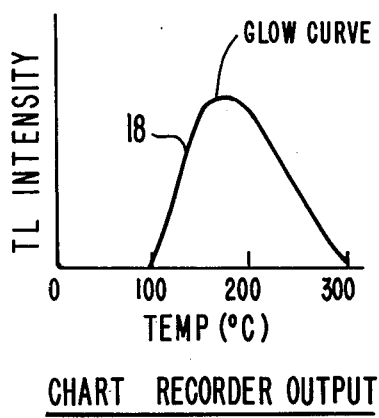
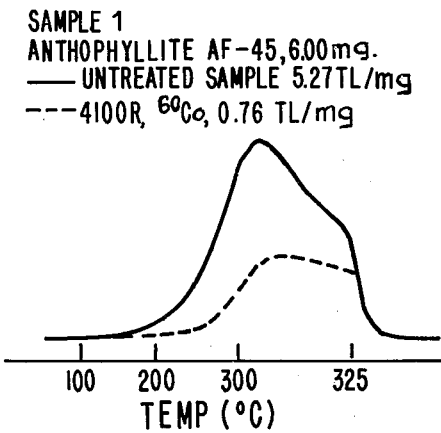

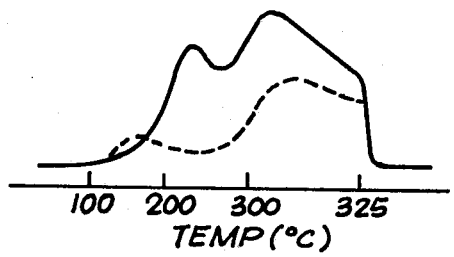
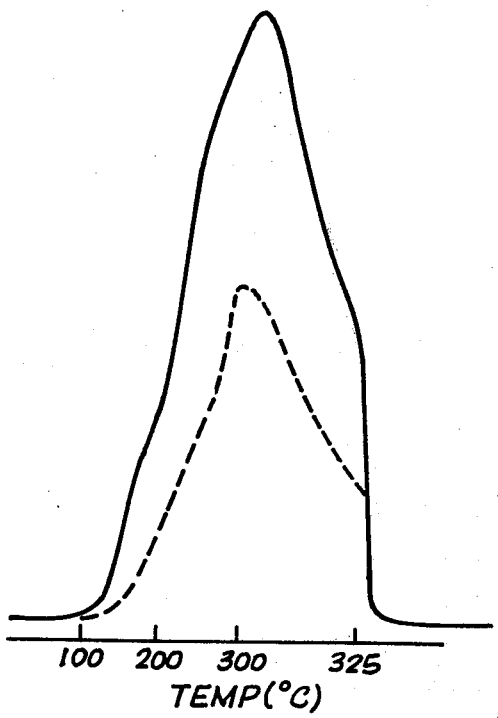
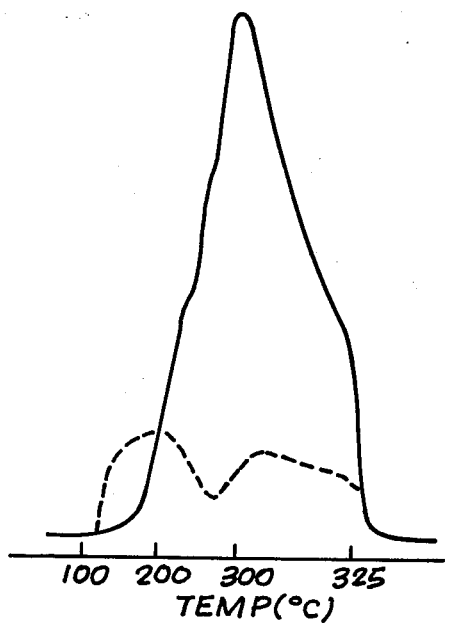
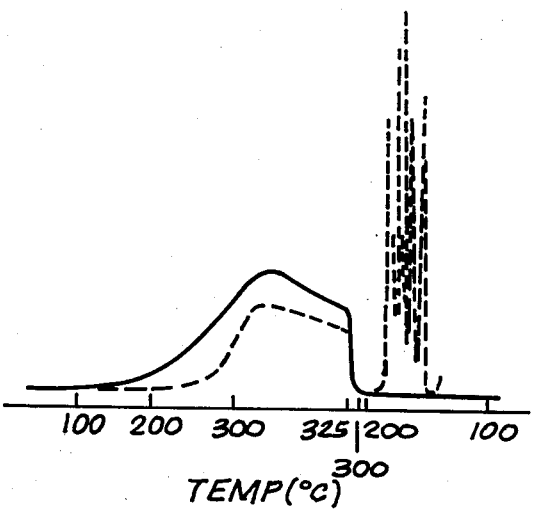

SAMPLE 6
CHRYSOTILE 15-5, 6.07 mg
— UNTREATED SAMPLE 49.01 TL/mg
--- 4100R, $^{60}$Co, 10.50 TL/mg

SAMPLE 7
GRUNERITE FIBROUS 5.72 mg
— UNTREATED SAMPLE 0.44 TL/mg
--- 4100R, $^{60}$Co, 0.14 TL/mg

SAMPLE 8
GRUNERITE NON-FIBROUS 20.84 mg
— UNTREATED SAMPLE 0.33 TL/mg
--- 4100R, $^{60}$Co, 0.19 TL/mg

SAMPLE 9
TREMOLITE FIBROUS 5.86 mg
— UNTREATED SAMPLE 8.12 TL/mg
--- 4100R, $^{60}$Co, 1.73 TL/mg

SAMPLE 10
TREMOLITE T-77, 4.89 mg
— UNTREATED SAMPLE 1.42 TL/mg
--- 4100R, $^{60}$Co, 0.15 TL/mg

METHOD OF ANALYSIS OF ASBESTIFORM MINERALS BY THERMOLUMINESCENCE

BACKGROUND OF THE INVENTION

The invention disclosed herein was made under, or in, the course of DOE Contract No. EY-76-C-03-0472 with the University of California.

The present invention relates to a method for identifying and quantifying asbestiform minerals using thermoluminescent analysis, and more particularly, it relates to a method whereby thermoluminescent analysis is performed before and after subjecting a mineral sample to annealing and ionizing radiation.

Some common prior art techniques for asbestiform mineral analysis include expensive and time consuming electron microscopy methods. Using these methods, analysis often requires a half day of sample preparation plus 2-6 hours of analysis time for a single sample. The electron microscopist must search his sample for fibers, determine their chemical composition by micro X-ray emission, and confirm identity by electron diffraction. The efforts of this tedious procedure may produce results which may vary by up to two orders of magnitude when compared with the results of other analysts.

Other prior art techniques for mineral identification include thermoluminescent techniques which consist of annealing, irradiation and heating samples to develop glow curves for comparison with established glow curves of known minerals. Such a technique is described in U.S. Pat. No. 3,388,252, issued June 11, 1968, to W. L. Medlin. However, such techniques when applied to asbestiform minerals is considered to be inadequate to establish accurate identification of the mineral. Moreover, none of the prior art methods provide for quantitative analysis of asbestiform minerals.

SUMMARY OF THE INVENTION

In brief the present invention relates to a method for identifying and quantifying asbestiform minerals, including the steps of heating a mineral sample through its range of thermoluminescence, detecting the amount of thermoluminescence as a function of sample temperature, annealing the sample, subjecting the sample to ionizing radiation, heating the sample a second time through its range of thermoluminescence and detecting the amount of thermoluminescence as a function of sample temperature during the second heating, comparing the data accumulated during the first and second heating with data established by the same method for known asbestiform minerals to identify the sample, and integrating the thermoluminescent response during at least one of the heating steps to determine the quantity of asbestiform in the sample.

It is an object of the invention to rapidly, inexpensively, and accurately identify and quantify asbestiform minerals.

Another object is to provide a practical method for identifying and quantifying asbestiform minerals found in geological formations, human environments, and biological tissues.

Another object is to differentiate as to the source of otherwise similar asbestiform minerals.

Another object is to consistently identify and quantify asbestiform minerals.

Other objects and advantageous features of the invention will be apparent in a description of a specific embodiment thereof, given by way of example only, to enable one skilled in the art to readily practice the invention which is described hereinafter with reference to the accompanying drawings.

BRIEF DESCRIPTION OF THE DRAWINGS

FIG. 1 is a procedure flow chart illustrating exemplary steps of the method, according to the invention.

FIG. 2 is a diagrammatic cross-sectional view of a sample to be analyzed following the method of FIG. 1.

FIG. 3 is a diagrammatic view of some of the components of a thermoluminescence reader and shows the sample of FIG. 2 being heated to thermoluminescence.

FIG. 4 is a representative glow curve developed by means of a chart recorder with data derived from the thermoluminescence of the sample in the reader of FIG. 3.

FIGS. 5-15 are unique glow curve pairs for eleven samples of asbestiform minerals established as known by the procedure of the invention.

DETAILED DESCRIPTION OF THE INVENTION

Figure 10:
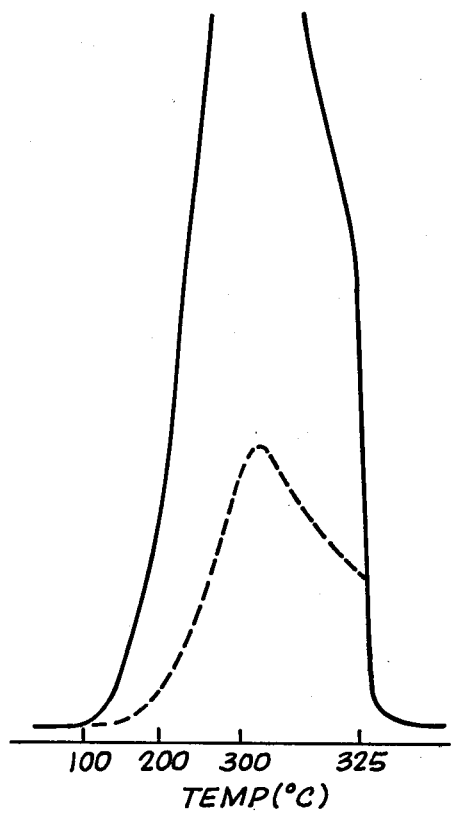

Reference will now be made in detail to a preferred procedure of the invention, an example of which is illustrated in the accompanying drawing. While the invention will be described in connection with a preferred procedure, it will be understood that it is not intended to limit the invention to that procedure. On the contrary, it is intended to cover all alternatives, modifications and equivalents as may be included within the spirit and scope of the invention as defined by the appended claims.

Referring now to the drawing, there is shown in FIG. 1 a flow chart illustrating exemplary steps A-E of the invention. More specifically, during Step A a sample mineral 10 (FIG. 2) is placed in a holder 11 which may be a tantalum weighing boat of approximately 0.15 grams (1.8×0.5×0.2 cm). Prior to loading the boat with the mineral, the boat is washed by rinsing with water, sonicated in an ethanol bath for five minutes, rinsed with dilute nitric acid, rinsed with double distilled water and let dry. The boat is then weighed on a microbalance to 0.01 mg. The mineral sample is then placed in the boat, spread uniformly in the bottom, and if of a fibrous nature, gently packed with a clean spatula and weighed again on the microbalance. The sample weight is then determined. Care is taken to handle the weighing boats only with clean forceps, and a dust cover is in place over the sample carrier to prevent contamination from atmospheric and/or room dusts.

During Step B (FIG. 1), the sample 11 is analyzed for thermoluminescence (TL) by using a thermoluminescence reader 13 which is shown diagrammatically in FIG. 3, including a heater 14 and a photomultiplier tube 16. During the analysis, a glow curve 18 (FIG. 4) for temperature versus thermoluminescence is developed on a chart recorder 20 which records TL intensity vs. applied temperature.

In an actual practice of the method a Harshaw Thermoluminescence Detector model 2000A, a Harshaw Automatic Integrating Picoammeter model 2000B, and a dual pen Rikadenki Kogyo Company chart recorder model B-261 were used for the analysis. In this practice the weighing boat 11 was placed on a permanent planchet with a 0.3×0.3×0.2 cm depression. The sample was analyzed by heating the planchet through the thermoluminescence range at a linear rate of 4.2° C./second from 100° C. to 300° C. and at a nonlinear rate up to 320° C. in a total period of 100 seconds. The resulting signal response from the photomultiplier tube 16 was integrated during the 100° C.–300° C. interval in the auto range mode, and a chart recording at a rate of 5 cm/minute obtained throughout the heating period. Throughout the analysis procedure N$_2$ gas was flowing through the detector at a rate of 0.3 SCFM.

During Step C the mineral is annealed by placing it in an annealing oven 22 such as a small muffle furnace at 400° C. for one hour followed immediately by two hours at 100° C. in a laboratory oven. The annealing procedure is necessary to assure that all the TL is removed from the sample that may still be present after the initial TL analysis. In this way it is ensured that subsequent TL is due to subsequent irradiation.

During Step D, $^{60}$Co Gamma-irradiation of the sample is performed by placing the weighing boat in a $^{60}$Co field for a length of time determined by calibration against such as a Victoreen condenser-R meter model 553 to give a total exposure of 4100R.

In Step E, the irradiated sample is then analyzed for TL by the previous procedure of Step A.

Figure 11:
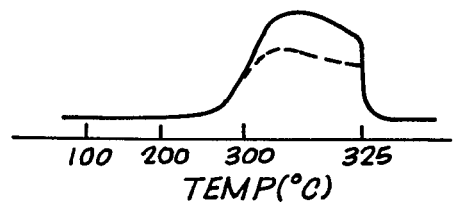
Figure 12:
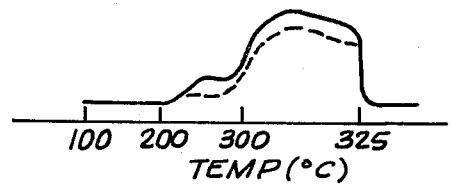
Figure 13:
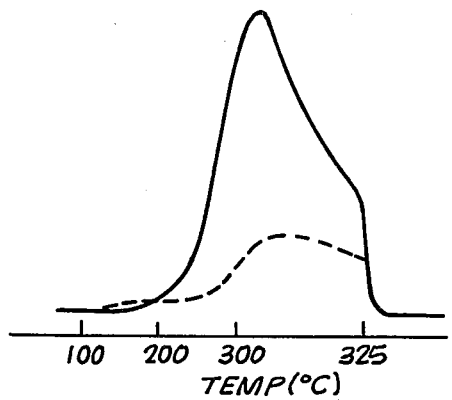
Figure 14:
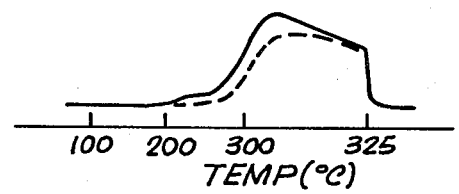
Figure 15:
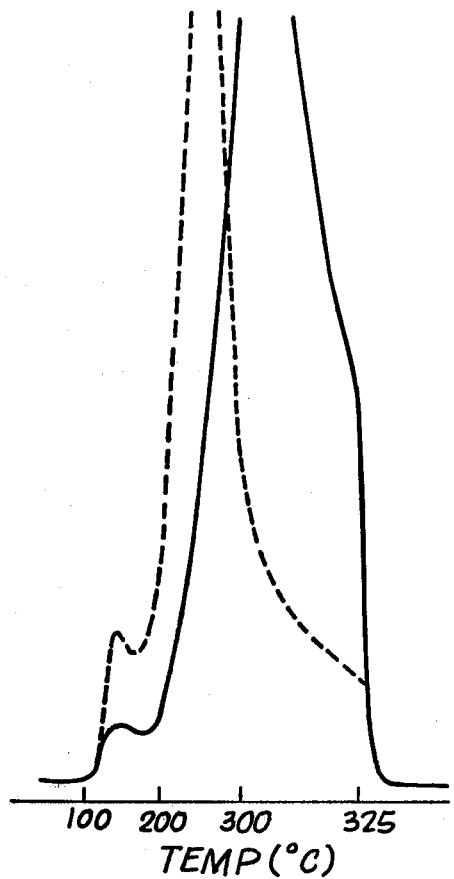

In the foregoing manner, two thermoluminescent "glow" curves are obtained: (1) prior to annealing and $^{60}$Co irradiation; and (2) subsequent to the annealing and irradiation. The two glow curves comprise a pair having unique shapes which may be compared with unique curve pairs of asbestiform minerals that have been previously established as known by the procedure of the invention using the same parameters, i.e., equal sample weights, time periods, temperatures, and ionizing radiation. In this way mineral samples may be rapidly, inexpensively and accurately analyzed to identify asbestiform minerals. In FIGS. 5–15 eleven unique pairs of glow curves are shown that have been established using the procedure of the invention for eleven common asbestiform minerals. For each curve, there is also a statement above the curve regarding the quantity of thermoluminescence per unit mass of the sample both before and after annealing and irradiation. This quantity is derived from signal integration for the 100°–300° C. linear heating period of the sample and may be used as an additional characteristic to rapidly identify unknown samples for the listed asbestiform minerals. The quantity of asbestiform mineral found in a sample also may be used in correlating the sample with a particular source from among more than one source of the same species of asbestiform mineral. This is an especially valuable feature of the invention when it is used for environmental monitoring or analysis in order to determine from which of several possible sources the asbestiform mineral may be emanating.

The utilization of thermoluminescent techniques for the rapid and inexpensive identification and quantification of asbestiform minerals as used in this invention is predicated on an empirical theory that asbestiform minerals are basically doped crystals similar to those presently used in radiation dosimetry. Similar techniques also are routinely used in dating crystalline archaeological materials, whereby the radiation history of asbestiform minerals from exposure to ionizing radiation throughout geologic time corresponds to the thermoluminescence of the sample. In this theory, naturally occurring lattice imperfections, or imperfections created by selective doping, result in localized charged centers within the crystal lattice. Ionizing radiation produces free electrons within the crystal, and some of these electrons wander in the conduction band and recombine rapidly (radiophotoluminescence). Other electrons and their holes may be trapped at energies below the conduction band. Freeing of these trapped electrons will result in a luminescent recombination with a positive hole. In thermoluminescence the probability of an electron escaping the trap and subsequently undergoing luminescent recombination is related to the atomic vibrations within the crystal and therefore can be represented simply as follows:

$$p = se^{-E/kT}$$

where: p is the probability of electrons escaping from the trap;

s is the atomic vibration correction factor;

E is the energy depth of the trapped electron below the conduction band; and

T is absolute temperature.

Therefore, thermoluminescent materials store the ionizing radiation history of the sample, and subsequent reading of this history is afforded by thermally induced photoluminescence.

In actual performance of the invention, using the techniques described hereinbefore and the established glow curve characteristics shown in FIGS. 5–15, nine unknown asbestos samples and two unknown tremolite mixtures were analyzed in a double-blind study. Of the eleven unknowns analyzed, ten were correctly identified and the eleventh (item #9) was partially identified with the procedure of the invention. The results of this analysis is summarized in Table I.

TABLE I

IDENTIFICATION OF ASBESTIFORM MINERALS FROM GLOW CURVE CHARACTERISTICS

| Unknown # | Experimental Identification | Actual Mineral |
|---|---|---|
| 1 | Tremolite T-79 | Tremolite T-79 |
| 2 | Tremolite TF-48 | Tremolite TF-48 |
| 3 | Anthophyllite A-102 | Anthophyllite A-102 |
| 4 | Tremolite T-77 | Tremolite T-77 |
| 5 | Chrysotile CH-29 | Chrysotile CH-29 |
| 6 | Antigorite | Antigorite |
| 7 | Grunerite-fibrous | Grunerite-fibrous |
| 8 | Grunerite-non-fibrous | Grunerite-non-fibrous |
| 9 | Tremolite T-79 + other Tremolite | Tremolite T-79 + Tremolite T-48 |
| 10 | Tremolite T-77 Tremolite TF-48 | Tremolite T-77 + Tremolite TF-48 |
| 11 | Anthophyllite AF-45 | Anthophyllite AF-45 |

Thermoluminescent analyses of asbestiform minerals in accordance with the procedure of the invention provides a rapid, inexpensive method for qualitative and quantitative analysis. It also provides a means for improved identification of complex mixtures of asbestiform and other minerals particularly of environmental samples where sensitivity for microgram quantities for many materials is required. In addition, it is envisioned that the invention will be used for biological tissue analyses. Also, the invention may be used to distinguish between asbestiform minerals of the same species, but from different geological sources, by correlating the thermoluminescence per unit mass of a mineral and the glow curve patterns with the source of the mineral. Thus, thermoluminescent analysis of asbestiform minerals should be of particular aid in identifying the origin of ambient minerals.

While an embodiment of the invention has been shown and described, further embodiments or combinations of those described herein will be apparent to those skilled in the art without departing from the spirit of the invention.

What is claimed is:

1. A method of analysis of an untreated sample for asbestiform minerals, comprising the steps of:
    heating the untreated sample during a first time period;
    detecting the amount of thermoluminescence of the sample during heating as a function of sample temperature during the first time period;
    annealing the sample following said detection step to exhaust all thermoluminescence of the sample;
    subjecting the sample to ionizing radiation following said annealing;
    heating the sample during a second time period following said ionizing radiation of the sample; and
    detecting the amount of thermoluminescence of the sample as a function of sample temperature during heating during the second time period.

2. The method of claim 1, further including the step of:
    integrating the amount of thermoluminescence over a predetermined period of at least one of said heating steps.

3. The method of claim 2, wherein said heating step is during said first time period.

4. The method of claim 2, wherein the heating is linear during said integrating.

5. The method of claim 1, further including, during a first procedure of claim 1, establishing first and second glow curves, corresponding to the detecting during the first and second time periods, for a known asbestiform mineral sample, for comparison with corresponding first and second glow curves, derived during a second procedure of claim 1 using identical parameters and corresponding to the detecting during first and second time periods of the second procedure for an unknown mineral sample.

6. The method of claim 1, wherein the heating during the first time period is at a linear rate of 4.2° C. per second from 100° C. to 300° C. and at a nonlinear rate up to 320° C., the first time period having a length of 100 seconds.

7. The method of claim 1, wherein the annealing of the sample is in a muffle furnace at 400° C. for one hour followed by two hours at 100° C. in a laboratory oven.

8. The method of claim 1, wherein the sample is subjected to the ionizing radiation of a $^{60}$Co source for a total exposure of 4100 R.

9. The method of claim 1, wherein the sample is taken from a human environment.

10. The method of claim 1, wherein the sample is biological tissue.

11. The method of claim 1, wherein the sample is taken directly from a geological formation.

* * * * *